United States Patent [19]

Debaert et al.

[11] Patent Number: 5,162,364

[45] Date of Patent: Nov. 10, 1992

[54] 4-AMINOBUTYRIC ACID COMPOUNDS, COMPOSITIONS, AND METHOD OF USE FOR TREATING DISORDERS RELATED TO A DYSFUNCTION OF GABA$_B$ RECEPTORS

[75] Inventors: Michel Debaert, Lille; Pascal Berthelot, Haubourdin; Claude Vaccher, Wattignies, all of France

[73] Assignee: Adir et Compagnie, Courbevoie, France

[21] Appl. No.: 713,760

[22] Filed: Jun. 11, 1991

[30] Foreign Application Priority Data

Jun. 27, 1990 [FR] France .................. 90 08093

[51] Int. Cl.$^5$ .................. A61K 31/34; A61K 31/38; C07D 307/78; C07D 333/52
[52] U.S. Cl. .................. 514/438; 514/443; 514/445; 514/447; 514/469; 514/471; 514/472; 549/51; 549/57; 549/58; 549/62; 549/63; 549/65; 549/68; 549/75; 549/76; 549/467; 549/478; 549/479; 549/480; 549/481; 549/493; 549/494; 549/496
[58] Field of Search ............... 549/467, 496, 479, 478, 549/481, 480, 63, 65, 68, 75, 76, 493, 494; 514/469, 471, 472, 438, 443, 445, 447

[56] References Cited

PUBLICATIONS

Berthelot et al., *J. Med. Chem.*, vol. 30, No. 4, pp. 743-746 (1987).
Chemical Abstracts, vol. 106, entry 176087e, 1987.
Chemical Abstracts, vol. 111, entry 50294e, 1989.
Chemical Abstracts, vol. 111, entry 50265w, 1989.
Berthelot et al., Poster, Symposium upon GABA$_B$ Receptors in Cambridge, UK, 1989.

*Primary Examiner*—Mary C. Lee
*Assistant Examiner*—Lenora A. Miltenberger
*Attorney, Agent, or Firm*—Gordon W. Hueschen

[57] ABSTRACT

A compound of formula (I):

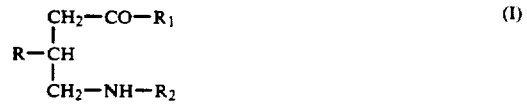

in which R, R$_1$ and R$_2$ are as defined in the description.
Medicinal product, which is useful in treating disorders related to a dysfunction of GABA$_B$ receptors.

16 Claims, No Drawings

4-AMINOBUTYRIC ACID COMPOUNDS, COMPOSITIONS, AND METHOD OF USE FOR TREATING DISORDERS RELATED TO A DYSFUNCTION OF $GABA_B$ RECEPTORS

The invention relates to new 4-aminobutyric acid compounds.

Numerous arylpropionic compounds are known from the literature that have, in particular, analgesic and anti-inflammatory properties. Also known is baclofen or 4-amino-3-(4-chlorophenyl)butyric acid, a compound agonistic to $GABA_B$ receptors which is used in human therapeutics on account of its antispastic properties. Other 4-amino-3-arylbutyric acids, especially heteroarylbutyric compounds, which exhibit an affinity to the $GABA_B$ receptor, have also been described (J. Med. Chem. 1987, 30, 743-746).

In comparison with the compounds of the prior art, the compounds of the present invention exhibit a very selective and distinctly greater affinity. In addition, some of them antagonise the excitation induced by convulsants at doses lower than that of baclofen. Others exhibit the property of stimulating the synthesis of cyclic AMP in the cerebral cortex, and therefore of increasing the metabolic capacities of the brain. The intensity of that affinity to the $GABA_B$ receptor and the strength of their activity renders possible, in human or animal therapeutics, the administration of lower doses of the compounds of the invention. This reduced dosage goes hand in hand with a reduction in the side effects that are observed with less active compounds since it is generally recognised that toxicity has no connection with the mechanism of pharmacological action but depends essentially on the chemical structure of the compounds. Thus, small amounts of the compounds of the invention produce an effect comparable to that obtained with much greater amounts of the compounds of the prior art; the risks of toxic effects, especially hepatic ones, are greatly reduced. That advantage is particularly valuable in the case of the weak populations for which the compounds are intended, generally individuals suffering from spastic disorders or elderly individuals (Alzheimer's disease, individuals suffering from senile dementia or affected by disorders connected with senescence), these populations often already suffering from disorders of the hepatic functions.

More specifically, the invention relates to new 4-aminobutyric acid compounds corresponding to the general formula (I):

$$\begin{array}{c} CH_2-CO-R_1 \\ | \\ R-CH \\ | \\ CH_2-NH-R_2 \end{array} \qquad (I)$$

in which:

$R_1$ represents a hydroxy, amino, lower alkylamino or lower alkoxy group, or a halogen atom, $R_2$ represents a hydrogen atom, a lower alkyl radical, a lower acyl radical, or a lower alkoxycarbonyl radical, R represents:
a radical of the formula

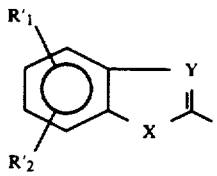

in which:

X represents an oxygen or sulphur atom or an NH group,

Y represents a —CH—, oxygen, or nitrogen, $R'_1$ and $R'_2$, which are identical or different represent a halogen or hydrogen atom or a lower alkyl, lower alkoxy, hydroxy, nitro, amino, lower alkylamino or trifluoromethyl radical, with the proviso that, when X is an oxygen atom, Y is —CH— and each of $R'_1$ and $R_2$ is a hydrogen atom, then $R'_2$ can represent neither a hydrogen atom nor a methoxy group, a radical of the formula

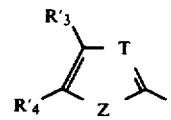

in which:

Z represents an oxygen or sulphur atom or an NH group,

T represents —CH— or nitrogen, $R'_3$ and $R'_4$, which are identical or different, represent a radical selected from hydrogen, halogen, lower alkyl, lower alkoxy, hydroxy, nitro, amino, lower alkylamino or trifluoromethyl, with the proviso that, when Z is a sulphur atom, T is —CH— and $R'_3$ is a hydrogen atom, $R'_4$ may not be a methyl grouping or a hydrogen, chlorine or bromine atom, and that, when Z is an oxygen atom, T is —CH— and $R'_3$ is a hydrogen atom, $R'_4$ may not be a hydrogen atom or a methyl group, a cycloalkyl radical having 4 or 5 carbon atoms or a cycloalkylalkyl or dicycloalkylalkyl radical having from 4 to 16 carbon atoms, optionally substituted at rings level by a group selected from halogen, hydroxy, lower alkyl, lower alkoxy, nitro, amino, lower alkylamino or trifluoromethyl, an optionally substituted aromatic radical having 6 ring members that includes 2 or 3 nitrogen atoms in its carbon skeleton, an aromatic radical having 6 ring members that includes from 1 to 3 nitrogen atoms in its carbon skeleton and is fused to a benzene ring, it being optionally possible for each of these 2 rings to be substituted, or a saturated or unsaturated ring having seven ring members that includes one or two nitrogen atoms in its carbon skeleton and is optionally fused to a benzene ring and is optionally substituted on the nitrogen and/or benzene ring, the term "substituted" indicating that the groups so qualified can be substituted by one or more groups selected from halogen atom, lower alkyl, lower alkoxy, hydroxy, trifluoromethyl, nitro, amino or lower alkylamino their optical isomers and also, where appropriate, their salts of addition with a pharmaceutically acceptable base or acid, it being understood that, unless otherwise indicated, the terms "lower alkyl", "lower alkoxycarbonyl", "lower alkoxy", "lower alkylamino" and "lower acyl" indicate groups containing from 1 to 6 carbon atoms in a straight or branched chain.

Of the pharmaceutically acceptable acids or bases that can be used to convert the compounds of the invention into salts there may be mentioned, by way of non-limiting examples, hydrochloric, hydrobromic, sulphuric, nitric, oxalic, malic, maleic, succinic, tartaric, methanesulphonic, camphoric and camphosulphonic acid, sodium hydroxide, potassium hydroxide, triethylamine, diethylamine, ethanolamine, diethanolamine, arginine, and lysine.

The process for the preparation of the compounds of formula (I) is characterised in that there is used as starting material a compound of formula (II):

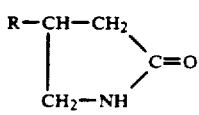

in which R is as defined in formula (I), which can be:

either hydrolysed by the action of a metal hydroxide to obtain, after optional purification, a compound of formula (I/a):

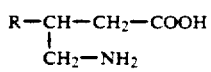

a particular form of the compounds of formula (I) in which $R_1$ represents a hydroxy group, $R_2$ represents a hydrogen atom and R is as defined in formula (I), or converted by the action of a lower alkyl dicarbonate in the presence of a strong base into a compound of formula (III):

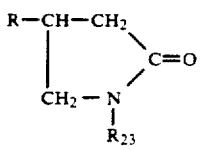

in which R is as defined above and $R_{23}$ represents a lower alkoxycarbonyl group, which is treated, after optional purification, with an alkali metal hydroxide in an anhydrous medium, and then with an acid to obtain a compound of formula (I/b):

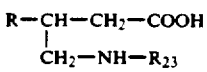

in which R and $R_{23}$ are as defined above, a particular form of the compounds of formula (I) in which $R_1$ represents a hydroxy group, $R_2$ represents a lower alkoxycarbonyl radical and R is as defined in formula (I), which, treated in an acidic medium, yields a compound of formula (I/a) such as defined above, which compound of formula (I/a), irrespective of the process by which it has been obtained, may, if desired, be converted by a halogenating agent into its halide of formula (I/c):

in which Hal represents a halo9en atom and R is as defined in formula (I), a particular form of the compounds of formula (I) in which $R_1$ represents a halogen atom, $R_2$ represents a hydrogen atom and R is as defined in formula (I), which compound of formula (I/a) or (I/c) can be treated, if desired:

with a compound of the formula:

$$R_1''-H$$

in which $R_1''$ represents an amino, lower alkylamino or lower alkoxy group, to yield a compound of formula (I) in which $R_1$ represents an amino, lower alkylamino or lower alkoxy group, and, if desired, with an alkylating agent such as dimethyl sulphate or an alkyl halide of the formula:

$$R_{21}-X$$

in which $R_{21}$ represents a lower alkyl group and X represents a halogen atom, to yield a compound of formula (I) in which $R_2$ represents a lower alkyl group, or, if desired, with an acid chloride of the formula:

$$R_{22}Cl$$

or an acid anhydride of the formula:

$$R_{22}OR_{22}$$

$R_{22}$ representing a lower acyl grouping, to yield a compound of formula (I) in which $R_2$ represents a lower acyl group, the compounds of formula (I) then, if desired, being either resolved into their optical isomers and then converted into salts by the addition of a pharmaceutically acceptable base or acid, or converted directly into salts in racemic form by the addition of a pharmaceutically acceptable base or acid.

The compounds of formula (II) can be obtained:

either by condensing, in an aprotic apolar solvent, an aldehyde of formula (V):

$$R-CHO \quad (V)$$

in which R is as defined in formula (I), with a carboxymethylidenetriphenylphosphorane ester of formula (VI):

$$(C_6H_5)_3-P=CH-COOR' \quad (VI)$$

in which R' represents a lower alkyl radical, to obtain an ester of formula (VII):

$$R-CH=CH-COOR' \quad (VII)$$

in which R and R' are as defined above, which is condensed in a protic polar medium with nitromethane in the presence of a strong base, to obtain a compound of formula (VIII):

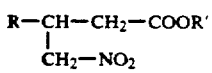  (VIII)

in which R and R' are as defined above, which is reduced in an alcoholic medium by the action of hydrogen in the presence of a metal catalyst, to form a compound of formula (IX):

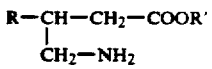  (IX)

in which R and R' are as defined above, which is cyclised by heating to form a compound of formula (II):

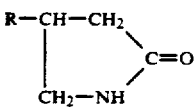  (II)

in which R is as defined in formula (I), or by treating a compound of formula (X):

RCOCH$_3$  (X)

in which R is as defined in formula (I), at elevated temperature and in the presence of zinc with a compound of formula (XI):

Br—CH$_2$—COOA  (XI)

in which A represents a lower alkyl grouping, to yield, after optional acidic hydrolysis, extraction and purification, a compound of formula (XII):

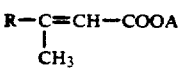  (XII)

in which R and A are as defined above, which is treated with N-bromosuccinimide to yield a compound of formula (XIII):

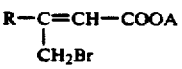  (XIII)

in which R and A are as defined above, which is treated with ammonia, preferably an excess thereof, to yield a compound of formula (XIV):

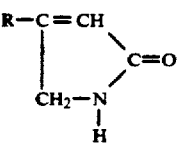  (XIV)

in which R is as defined above, which is subjected to catalytic hydrogenation to obtain a compound of formula (II) as defined above.

The compounds of formula (II), wherein R does not represent:

a 2-benzofuryl group substituted in the benzene nucleus by a chlorine atom, a bromine atom or a methoxy group, or a 2-benzothienyl group, and the compounds of formula (III) are new and are an integral part of the present invention in their capacity as starting materials that can be used for the synthesis of the compounds of the invention.

The compounds of formula (I) possess valuable pharmacological properties. They have a very great and selective affinity to the GABA$_B$ receptor, which is greater than that of the compounds of the prior art.

Some of them exhibit a GABA$_B$ receptor-antagonising activity and can therefore be administered in the treatment of memory disorders, mental disorders connected with senescence, and also in the treatment of Alzheimer's disease.

Other compounds, on the other hand, exhibit an agonist activity and are therefore suitable for spastic individuals or individuals suffering from Angina pectoris.

The present invention also relates to pharmaceutical compositions containing the compounds of formula (I) or one of their salts of addition with a pharmaceutically acceptable acid or base, alone or in combination with one or more pharmaceutically acceptable inert, non-toxic excipients or carriers.

Of the pharmaceutical compositions according to the invention there may be mentioned more particularly those that are suitable for oral, parenteral, nasal, rectal, perlingual, ocular or pulmonary administration, and especially injectable preparations, aerosols, eye or nose drops, tablets or dragées, sublingual tablets, soft gelatin capsules, sachets, suppositories, creams, ointments, and dermal gels.

The dosage varies according to the age and weight of the patient, the route of administration, the nature of the disorder and any associated treatment and ranges from 1 mg to 1 gram per 24 hours.

The following Examples illustrate the invention and do not limit it in any way.

The starting materials are described in the literature or can be prepared in a similar manner.

The 1H nuclear magnetic resonance spectra (NMR) were produced using tetramethylsilane (TMS) as the internal reference. The chemical displacements are expressed in parts per million (ppm).

The infrared spectra were effected in the form of potassium bromide discs containing approximately 1% of the product to be analysed.

EXAMPLE 1

3-(2-(5-isopropylbenzofuryl)) 4-aminobutanoic acid

STAGE A: ethyl 3-(2-(5-isopropylbenzofuryl))-propenoate

A solution containing 0.1 mol of 2-(5-isopropyl)benzofurylcarbaldehyde and 0.1 mol of ethoxycarbonylmethylidenetriphenylphosphorane in 200 cm$^3$ of benzene is heated under reflux for 4 hours under a nitrogen atmosphere. It is then cooled and the solvent is evaporated under reduced pressure. The residue is taken up in 200 cm$^3$ of ether, the insoluble material is removed by suction-filtering and the filtrate is evaporated to dryness and then the evaporation residue is distilled under reduced pressure. The compound of stage A is obtained: b.p. (3 mm Hg)=186° C.

STAGE B: ethyl 3-(2-(5-isopropylbenzofuryl))-4-nitrobutanoate 0.05 mol of the compound obtained in stage A of Example 1 is heated for 18 hours at 70° C. in 50 cm³ of nitromethane and 2 cm³ of a 40% methanolic solution of Triton B. The whole is cooled, neutralised with a molar solution of hydrochloric acid and extracted with ether. The ethereal phase is washed with water, dried, filtered and then evaporated to dryness. The compound of stage B is obtained after purification by high performance liquid chromatography.

STAGE C: 4-(2-(5-isopropylbenzofuryl))-2-oxopyrrolidine 0.05 mol of the compound obtained in stage B of Example 1 is reduced in an ethanolic solution by hydrogen at atmospheric pressure and at ambient temperature in the presence of Raney nickel. The whole is filtered and evaporated under reduced pressure, and then the residue is heated for 2 hours and recrystallised from petroleum ether.

Melting point: 151° C.
Spectral characteristics:
infrared: 1690 cm$^{-1}$: $\sigma$CO
3300 m$^{-1}$: $\sigma$NH
NMR (CDCl₃):
δ: 1.26 ppm: doublet: ((CH₃)₂C)
δ: 2.75 ppm: doublet: (CH₂ CO)
δ: 2.80–3.20 ppm: multiplet: (CH(CH₃)₂)
δ: 3.40–4.10 ppm: multiplet: (CH, CH₂ N)
δ: 5.70 ppm: singlet: (NH)
δ: 6.50 ppm: singlet: (H₃', benzofuran)
δ: 7.00–7.50 ppm: multiplet: (H₄', H₆', H₇'; benzofuran)

STAGE D: 3-(2-(5-isopropylbenzofuryl))-4-aminobutanoic acid 0.01 mol of the compound obtained in stage C of Example 1 is heated under reflux for one hour in 20 cm³ of 95% ethanol in the presence of 5 cm³ of 40% sodium hydroxide solution. The whole is cooled and evaporated to dryness. The residue is taken up in from 15 to 20 cm³ of water that has been acidified to pH=1 by 10% HCl. The whole is evaporated to dryness, taken up in from 1 to 3 cm³ of trifluoroacetic acid and chromatographed over an ion exchange resin (DOWEX 50 WH+) using a 5% ammonium hydroxide solution as eluant. The eluant is evaporated to dryness and the residue is recrystallised from ethanol.

Melting point: 190° C.
Spectral characteristics:
infrared: 1580 cm$^{-1}$: $\sigma$CO
2500–3200 cm$^{-1}$: $\sigma$OH

EXAMPLE 2

3-(2-(5-methylbenzofuryl))-4-aminobutanoic acid

By following the instructions in stages A to D of Example 1, but replacing the 2-(5-isopropyl)benzofurylcarbaldehyde in stage A of Example 1 by 2-(5-methyl)-benzofurylcarbaldehyde, there are obtained in succession, after a purification stage by high performance liquid chromatography, as appropriate, the following compounds:

STAGE A: ethyl 3-(2-(5-methylbenzofuryl))-propenoate
Melting point: 73° C.
STAGE B: ethyl 3-(2-(5-methylbenzofuryl))-4-nitrobutanoate STAGE C: 4-(2-(5-methylbenzofuryl))-2-oxopyrrolidine
Melting point: 151° C.
Spectral characteristics:
infrared: 1690 cm$^{-1}$: $\sigma$CO
3300 m$^{-1}$: $\sigma$NH
NMR (CDCl₃):
δ: 2.41 ppm: singlet: (CH₃)
δ: 2.69 ppm: doublet: (CH₂CO)
δ: 3.50–4.10 ppm: multiplet: (CH₂N, CH)
δ: 6.00 ppm: singlet: (NH)
δ: 6.46 ppm: singlet: (H₃', benzofuran)
δ: 6.90–7.50 ppm: multiplet: (H₄', H₆', H₇'; benzofuran)

STAGE D: 3-(2-(5-methylbenzofuryl))-4-aminobutanoic acid
Melting point: 191° C.
Spectral characteristics:
infrared: 1580 cm$^{-1}$: $\sigma$CO
2300–3200 cm$^{-1}$: $\sigma$(COO—, NH₃+)

EXAMPLE 3

3-(2-(5-ethylbenzofuryl))-4-aminobutanoic acid

By following the instructions in stages A to D of Example 1, but replacing the 2-(5-isopropyl)benzofurylcarbaldehyde in stage A of Example 1 by 2-(5-ethyl)-benzofurylcarbaldehyde, there are obtained in succession, after a purification stage by high performance liquid chromatography, as appropriate, the following compounds:

STAGE A: ethyl 3-(2-(5-ethylbenzofuryl))propenoate
Melting point: 52° C.
STAGE B: ethyl 3-(2-(5-ethylbenzofuryl))-4-nitrobutanoate
STAGE C: 4-(2-(5-ethylbenzofuryl))-2-oxopyrrolidine
Melting point: 125°–127° C.
Spectral characteristics:
infrared: 1670 cm$^{-1}$: $\sigma$CO 3200 m$^{-1}$: $\sigma$NH
NMR (CDCl₃):
δ: 1.25 ppm: triplet: (CH₂—CH₃)
δ: 2.50–3.00 ppm: multiplet: (CH₂—CH₃, CH₂CO)
δ: 3.40–4.10 ppm: multiplet: (CH₂N, CH)
δ: 5.93 ppm: singlet: (NH)
δ: 6.46 ppm: singlet: (H₃', benzofuran)
δ: 7.00–8.00 ppm: multiplet: (H₄', H₆', H₇'; benzofuran)

STAGE D: 3-(2-(5-ethylbenzofuryl))-4-aminobutanoic acid
Melting point: 195° C.
Spectral characteristics:
infrared: 1580 cm$^{-1}$: $\sigma$CO
2300–3200 cm$^{-1}$: $\sigma$OH

EXAMPLE 4

3-(2-(5-(1-methylpropyl)benzofuryl))-4-aminobutanoic acid

By following the instructions in stages A to D of Example 1, but replacing the 2-(5-isopropyl)benzofurylcarbaldehyde in stage A of Example 1 by 2-(5-(1-methylpropyl))benzofurylcarbaldehyde, there are obtained in succession, after a purification stage by high performance liquid chromatography, as appropriate, the following compounds:

STAGE A: ethyl 3-(2-(5-(1-methylpropyl)benzofuryl))propenoate b.p. (0.5 mm Hg) = 165° C.

STAGE B: ethyl 3-(2-(5-(1-methylpropyl)benzofuryl))-4-nitrobutanoate

STAGE C: 4-(2-(5-(1-methylpropyl)benzofuryl))-2-oxopyrrolidine

Melting point: 111°-113° C.
Spectral characteristics:
infrared: 1700 cm$^{-1}$: σCO
3200 m$^{-1}$: σNH
NMR (CDCl$_3$):
δ: 0.80 ppm: triplet: (CH$_3$—CH$_2$—)
δ: 1.28 ppm: doublet: ($\overline{CH}_3$—CH—)
δ: 1.45–1.80 ppm: multiplet: (—CH$_2$—CH)
δ: 2.68 ppm: doublet: (CH$_2$CO)
δ: 3.50–4.10 ppm: multiplet: (CH$_2$N, CH)
δ: 5.66 ppm: singlet: (NH)
δ: 6.49 ppm: singlet: (H$_3$', benzofuran)
δ: 7.00–7.50 ppm: multiplet (H$_4$', H$_6$', H$_7$'; benzofuran)

STAGE D: 3-(2-(5-(1-methylpropyl)benzofuryl))-4-aminobutanoic acid

Melting point: 200° C.
Spectral characteristics:
infrared: 1580 cm$^{-1}$: σCO 2300–3200 cm$^{-1}$: σOH

EXAMPLE 5

3-(2 (5-fluorobenzofuryl))-4-aminobutanoic acid

By following the instructions in stages A to D of Example 1, but replacing the 2-(5-isopropyl)benzofurylcarbaldehyde in stage A of Example 1 by 2-(5-fluoro)-benzofurylcarbaldehyde, there are obtained in succession, after a purification stage by high performance liquid chromatography, as appropriate, the following compounds:

STAGE A: ethyl 3-(2-(5-fluorobenzofuryl))propenoate

Melting point: 112° C.

STAGE B: ethyl 3-(2-(5-fluorobenzofuryl))-4-nitrobutanoate

STAGE C: 4-(2-(5-fluorobenzofuryl))-2-oxopyrrolidine

Melting point: 178°-180° C.
Spectral characteristics:
infrared: 1690 cm$^{-1}$: σCO
3200 m$^{-1}$: σNH
NMR (CDCl$_3$):
δ: 2.70 ppm: doublet: (CH$_2$ CO)
δ: 3.40–4.10 ppm: multiplet: (CH$_2$N, CH)
δ: 5.75 ppm: singlet: (NH)
δ: 6.50 ppm: singlet: (H$_3$'; benzofuran)
δ: 6.80–7.50 ppm: multiplet: (H$_4$', H$_6$', H$_7$'; benzofuran)

STAGE D: 3-(2-(5-fluorobenzofuryl))-4-aminobutanoic acid

Melting point: 200°-202° C.
Spectral characteristics:
infrared: 1580 cm$^{-1}$: σCO 2300–3200 cm$^{-1}$: σOH
NMR (D$_2$O):
δ: 2.76 ppm: doublet: (CH$_2$ CO)
δ: 3.30–4.00 ppm: multiplet: (CH$_2$N, CH)
δ: 6.88 ppm: singlet: (H$_3$'; benzofuran)
δ: 6.90–7.90 ppm: multiplet: (H$_4$', H$_6$', H$_7$'; benzofuran)

EXAMPLE 6

3-(2-(5-bromobenzofuryl))-4-aminobutanoic acid

By following the instructions in stages A to D of Example 1, but replacing the 2-(5-isopropyl)benzofurylcarbaldehyde in stage A of Example 1 by 2-(5-bromo)-benzofurylcarbaldehyde, there are obtained in succession, after a purification stage by high performance liquid chromatography, as appropriate, the following compounds:

STAGE A: ethyl 3-(2-(5-bromobenzofuryl))propenoate

STAGE B: ethyl 3-(2-(5-bromobenzofuryl))-4-nitrobutanoate

STAGE C: 4-(2-(5-bromobenzofuryl))-2-oxopyrrolidine

STAGE D: 3-(2-(5-bromobenzofuryl))-4-aminobutanoic acid

Melting point: 200°-202° C.
Spectral characteristics:
infrared: 1580 cm$^{-1}$: σCO
2300–3200 cm$^{-1}$: σOH
NMR (D$_2$O):
δ: 2.76 ppm: doublet: (CH$_2$ CO)
δ: 3.30–4.00 ppm: multiplet: (CH$_2$N, CH)
δ: 6.88 ppm singlet: (H$_3$'; benzofuran)
δ: 6.90–7.90 ppm: multiplet: (H$_4$', H$_6$', H$_7$'; benzofuran)

EXAMPLE 7

3-(2-(4,5-dichlorothienyl))-4-aminobutanoic acid

By following the instructions in stages A to D of Example 1, but replacing the 2-(5-isopropyl)benzofurylcarbaldehyde in stage A of Example 1 by 2-(4,5-dichloro)thienylcarbaldehyde, there are obtained in succession, after a purification stage by high performance liquid chromatography, as appropriate, the following compounds:

STAGE A: ethyl 3-(2-(4,5-dichlorothienyl))propenoate

Melting point: 76°-78° C.

STAGE B: ethyl 3-(2-(4,5-dichlorothienyl))-4-nitrobutanoate

STAGE C: 4-(2-(4,5-dichlorothienyl))-2-oxopyrrolidine

STAGE D: 3-(2-(4,5-dichlorothienyl))-4-aminobutanoic acid

Melting point: 188°-195° C.
Spectral characteristics:
infrared: 2500–3400 cm$^{-1}$: wide band (NH$_3$+,COO—)
1590 cm$^{-1}$: σCO
NMR (D$_2$O):
δ: 2.6 ppm: doublet: (CH$_2$ CO)
δ: 3.1–3.5 ppm: multiplet:

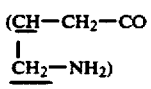

(C$\underline{H}$—CH$_2$—CO
|
$\underline{CH_2—NH_2}$)

δ: 7 ppm: singlet: (H ; thiophene)

EXAMPLE 8

3-(2-imidazolyl)-4-aminobutanoic acid

By following the instructions in stages A to D of Example 1, but replacing the 2-(5-isopropyl)benzofurylcarbaldehyde in stage A of Example 1 by 2-imidazolylcarbaldehyde, there are obtained in succession, after a purification stage by high performance liquid chromatography, as appropriate, the following compounds:

STAGE A: ethyl 3-(2-imidazolyl)propenoate
STAGE B: ethyl 3-(2-imidazolyl)-4-nitrobutanoate
STAGE C: 4-(2-imidazolyl)-2-oxopyrrolidine
Spectral characteristics:
infrared: 3200–3100 cm$^{-1}$: $\sigma$NH
NMR (DMSO):
δ: 2.5 ppm: doublet: (C$\underline{H}_2$ CO)
δ: 3.5 ppm: multiplet:

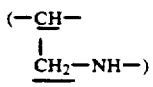

δ: 6.9 ppm: singlet: (H$_2$'; imidazole)
δ: 7.5 ppm: singlet: (NH—CO)
δ: 10–11 ppm: singlet: (NH; imidazole)
STAGE D: 3-(2-imidazolyl)-4-aminobutanoic acid
Melting point: 175°–180° C.
Spectral characteristics:
infrared: 2700–3400 cm$^{-1}$: $\sigma$(COO—, NH$_3$+)
1590 cm$^{-1}$: $\sigma$CO
NMR (D$_2$O):
δ: 2.6 ppm: doublet: (CH$_2$ CO) δ: 3.2–3.7 ppm: multiplet: (C$\underline{H}$—C$\underline{H}_2$—NH) δ: 7.05 ppm: singlet: (H$_2$': imidazole)

EXAMPLE 9

3-(2-(5-chlorobenzofuryl))-4-aminobutanoic acid

By following the instructions in stages A to C of Example 1, but replacing the 2-(5-isopropyl)benzofurylcarbaldehyde in stage A of Example 1 by 2-(5-chloro)-benzofurylcarbaldehyde, the following compounds are obtained in succession:

STAGE A: ethyl 3-(2-(5-chlorobenzofuryl))propenoate
STAGE B: ethyl 3-(2-(5-chlorobenzofuryl))-4-nitrobutanoate
STAGE C: 4-(2-(5-chlorobenzofuryl))-2-oxopyrrolidine
STAGE D: 1-tert.-butoxycarbonyl-2-oxo-4-(2-(5-chlorobenzofuryl))pyrrolidine 0.01 mol of triethylamine, 0.02 mol of di-tert.-butyl dicarbonate and 0.01 mol of dimethylaminopyridine are added under a nitrogen atmosphere and at ambient temperature to 0.01 mol of the compound obtained in stage C of Example 9 in solution in 50 cm$^3$ of methylene chloride. The reaction mixture is stirred for 7 hours and then evaporated to dryness. The residue obtained is taken up in 25 cm$^3$ of ether and the precipitate formed is removed by filtration. The ethereal phase is washed with water, dried and recrystallised from diisopropyl ether.
Melting point: 123° C.
Spectral characteristics:
infrared: 3100 cm$^{-1}$: $\sigma$NH
1800 cm$^{-1}$: $\sigma$CO (tert.-butoxycarbonyl)
1690 cm$^{-1}$: $\sigma$CO (lactam)
NMR (CDCl$_3$):
δ: 1.5 ppm: singlet: (tert.-butoxycarbonyl)
δ: 2.9 ppm doublet: (CH$_2$—CO)
δ: 4 ppm: multiplet: (C$\underline{H}$—C$\underline{H}_2$—N)
δ: 6.5 ppm: singlet: (H$_3$'; benzofuran)
δ: 7.15 ppm: doublet: (H$_6$'; benzofuran)
δ: 7.25 ppm doublet (H$_7$'; benzofuran)
δ: 7.5 ppm: doublet: (H$_4$'; benzofuran)

STAGE E: 4-tert.-butoxycarbonylamino-3-(2-(5-chlorobenzofuryl))butanoic acid 0.01 mol of a molar solution of lithium hydroxide is added at ambient temperature to 0.01 mol of the compound obtained in stage D of Example 9 in solution in tetrahydrofuran. The reaction mixture is stirred for thirty minutes, the solvent is evaporated, the residue is taken up in 25 cm$^3$ of water and then acidified with a 10% acetic acid solution. The whole is extracted with ether, dried, filtered, evaporated and recrystallised from hexane.
M.p. °C.: 104° C.
STAGE F: 3-(2-(5-chlorobenzofuryl))-4-aminobutanoic acid A mixture of 0.005 mol of the compound obtained in stage E of Example 9 and 0.25 mol of trifluoroacetic acid in 100 cm$^3$ of dichloromethane is stirred for one hour at ambient temperature and then evaporated to dryness. The residue is taken up in 25 cm$^3$ of water and then acidified to pH=1 with a solution of 10% hydrochloric acid, taken up in from 1 to 3 cm$^3$ of trifluoroacetic acid, and chromatographed on an ion exchange resin (DOWEX 50 WH+) using a 5% ammonium hydroxide solution as eluant. The eluant is evaporated to dryness and the residue is recrystallised from water.
M.p. °C.: 190°–192° C.
IR: 2300–3300 cm$^{-1}$: $\sigma$(COO—, NH$_3$+)
1590 cm$^{-1}$: $\sigma$CO
NMR (D$_2$):
δ: 2.75 ppm: doublet, 2H: (CH$_2$—COOH)
δ: 3.25–4 ppm: multiplet—3H: (C$\underline{H}$—C$\underline{H}$—NH$_2$)
δ: 6.8 ppm: singlet—1H: (furan)
δ: 7.25–7.75 ppm: multiplet—3H: (benzene)

EXAMPLE 10

3-(2-benzothienyl)-4-aminobutanoic acid

By proceeding as in Example 9, but initially using 2-benzothienylcarbaldehyde in stage A of Example 9, there are obtained:
STAGE D: 1-tert.-butoxycarbonyl-2-oxo-4-(2-benzothienyl)pyrrolidine
and in STAGE F: the title product:
M.p. °C.: 192°–197° C.
IR: 2300–3200 cm$^{-1}$: $\sigma$(COO—, NH$_3$+)
1575 cm$^{-1}$: $\sigma$CO
NMR (D$_2$O): δ: 2.7 ppm doublet—2H: (CH$_2$—CO)
δ: 3.3–3.5 ppm: multiplet—2H: (C$\underline{H}_2$—NH$_2$)
δ: 3.75 ppm: multiplet—1H: (C$\underline{H}$)
δ: 7.25–8.10 ppm: multiplet—5H: (benzothiophene)

EXAMPLE 11

3-(2-(5-ethoxybenzofuryl))-4-aminobutanoic acid

By proceeding as in Example 9, but initially using 2-(5-ethoxy)benzofurylcarbaldehyde in stage A of Example 9, there are obtained:
STAGE C: 4-(2-(5-ethoxybenzofuryl)-2-oxopyrrolidine
Melting point: 146°–148° C.
Spectral characteristics:
infrared: 1675 cm$^{-1}$: $\sigma$CO
3250 cm$^{-1}$: $\sigma$NH
NMR (CDCl$_3$):
δ: 1.35 ppm: triplet: (O—CH$_2$—CH$_3$)
δ: 2.50–2.70 ppm: doublet: (CH$_2$, $\overline{C}$O)
δ: 3.50–4.10 ppm: multiplet: (CH$_2$ N, CH, O—CH$_2$—CH$_3$)
δ: 6.15 ppm: singlet: (NH)

δ: 6.47 ppm: singlet: (H$_3$'; benzofuran)
δ: 6.85 ppm: doublet: (H$_4$'; benzofuran)
δ: 7.00 ppm: doublet: (H$_6$'; benzofuran)
δ: 7.30 ppm: doublet: (H$_7$'; benzofuran)

STAGE D: 1-tert.-butoxycarbonyl-2-oxo-4-(2-(5-ethoxybenzofuryl))pyrrolidine
and in STAGE F: the title product:
Melting point: 200° C.
Spectral characteristics:
infrared: 2300–3200 cm$^{-1}$: σ(COO—, NH$_3$+) 1620 cm$^{-1}$: σCO NMR (D$_2$O): δ: 1.40 ppm: triplet: (CH$_3$), δ: 2.60: doublet: (CH$_2$CO), δ: 3.30–3.95 ppm: multiplet: (CH—CH$_2$—NH$_2$), δ: 4.10 ppm: quintuplet: (OCH$_2$), δ: 6.75 ppm: singlet: (H$_3$'; benzofuran), δ: 7.00 ppm: doublet: (H$_6$'; benzofuran), δ: 7.20 ppm: doublet: (H$_4$'; benzofuran)

EXAMPLE 12

3-(2-benzothiazolyl)-4-aminobutanoic acid

By proceeding as in Example 9, but initially using 2-benzothiazolylcarbaldehyde in stage A of Example 9, there are obtained:
STAGE C: 4-(2-benzothiazolyl)-2-oxopyrrolidine
STAGE D: 1-tert.-butoxycarbonyl-2-oxo-4-(2-benzothiazolyl)pyrrolidine
and in STAGE F: the title product.

EXAMPLE 13

3-(2-(5-trifluoromethylbenzofuryl))-4-aminobutanoic acid

By proceeding as in Example 9, but initially using 2-(5-trifluoromethyl)benzofurylcarbaldehyde in stage A of Example 9, there are obtained:
STAGE C: 4-(2-(5-trifluoromethylbenzofuryl))-2-oxopyrrolidine
STAGE D: 1-tert.-butoxycarbonyl-2-oxo-4-(2-(5-trifluoromethylbenzofuryl))pyrrolidine
and in STAGE F: the title product.

EXAMPLE 14

3-(2-(4-trifluoromethylthienyl))-4-amino butanoic acid

By proceeding as in Example 9, but initially using 2-(4-trifluoromethyl)thienylcarbaldehyde in stage A of Example 9, there are obtained:
STAGE C: 4-(2-(4-trifluoromethylthienyl))-2-oxopyrrolidine
STAGE D: 1-tert.-butoxycarbonyl-2-oxo-4-(2-(5-trifluorométhylthiényl))pyrrolidine
and in STAGE F: the title product.

EXAMPLE 15

3-dicyclopropylmethyl-4-aminobutanoic acid

By proceeding as in Example 9, but initially using 2-dicyclopropylmethylcarbaldehyde in stage A of Example 9, there are obtained:
STAGE C: 4-dicyclopropylmethyl-2-oxopyrrolidine
STAGE D: 1-tert.-butoxycarbonyl-2-oxo-4-dicyclopropylmethylpyrrolidine
and in STAGE F: the title product.

EXAMPLE 16

3-(2-imidazolyl)-4-aminobutanoic acid methyl ester

STAGE A: 3-(2-imidazolyl)-4-aminobutanoic acid chloride 0.01 mol of 3-(2-imidazolyl)-4-aminobutyric acid chloride is dissolved in 30 cm$^3$ of methylene chloride. 0.025 mol of thionyl chloride is added and the whole is stirred at ambient temperature for 2 hours. The reaction medium is evaporated and the residue is extracted twice with chloroform after being rendered alkaline. The chloroform phases are combined and dried over calcium chloride and the chloroform is evaporated off. The residue is recrystallised.

STAGE B: 3-(2-imidazolyl)-4-aminobutanoic acid methyl ester 0.01 mol of the compound obtained in stage A of Example 16 is dissolved in 30 cm$^3$ of pyridine. 1 cm$^3$ of methanol is added. The whole is heated under reflux for five hours, the reaction medium is evaporated in vacuo on a water bath. The residue is dried and purified by chromatography.

EXAMPLE 17

3-(2-imidazolyl)-4-aminobutyramide 0.01 mol of the 3-(2-imidazolyl)-4-aminobutanoic acid chloride obtained in Example 12, stage A, is dissolved in 50 cm$^3$ of chloroform. A current of ammonia is bubbled in over a period of 2 hours. The reaction medium is evaporated to dryness and the residue is recrystallised.

EXAMPLE 18

3-(2-imidazolyl)-4-amino-N-propylbutyramide 0.01 mol of the compound obtained in stage A of Example 16 is dissolved in 50 cm$^3$ of chloroform. 0.025 mol of propylamine is added and the whole is heated under reflux for 5 hours while stirring and then cooled. The reaction mixture is then evaporated to dryness and extracted twice with chloroform. The chloroform phases are combined and dried over calcium chloride and the solvent is evaporated in vacuo on a water bath. The residue is purified by chromatography.

EXAMPLE 19

3-(2-(5-isopropylbenzofuryl))-4-aminobutanoic acid methyl ester

By proceeding as in Example 16, but replacing the 3-(2-imidazolyl)-4-aminobutyric acid in stage A of Example 16 by 3-(2-(5-isopropylbenzofuryl))-4-aminobutyric acid, the title compound is obtained.

EXAMPLE 20

3-(2-(5-isopropylbenzofuryl))-4-methylaminobutanoic acid methyl ester 0.01 mol of the compound of Example 19 is dissolved in 100 cm$^3$ of chloroform. 0.011 mol of dimethyl sulphate is added dropwise. The whole is stirred for 3 hours and the organic phase is washed with water and dried. The organic phase is evaporated to dryness and the residue is purified by chromatography.

EXAMPLE 21

3-cyclopropylmethyl-4-aminobutanoic acid

By proceeding as in Example 1, but replacing the 2-(5-isopropyl)benzofurylcarbaldehyde in stage A of Example 1 by cyclopropylacetaldehyde, there are obtained:
in STAGE C: 4-cyclopropylmethyl-2-oxopyrrolidine,
and in STAGE D: the title compound.

EXAMPLE 22

3-(2-(4,5-dichloroimidazolyl))-4-aminobutanoic acid

By proceeding as in Example 1, but replacing the 2-(5-isopropyl)benzofurylcarbaldehyde in stage A of Example 1 by 2-(4,5-dichloro)imidazolylcarbaldehyde there are obtained:
in STAGE C: 4-(2-(4,5-dichloroimidazolyl))-2-oxopyrrolidine,
and in STAGE D: the title compound.

EXAMPLE 23

3-(2-(4-methylimidazolyl))-4-aminobutanoic acid

By proceeding as in Example 1, but replacing the 2-(5-isopropyl)benzofurylcarbaldehyde in stage A of Example 1 by 2-(4-methyl)imidazolylcarbaldehyde there are obtained:
in STAGE C: 4-(2-(4-methylimidazolyl))-2-oxopyrrolidine,
and in STAGE D: the title compound.

EXAMPLE 24

3-(2-(4,5 dichlorofuryl))-4-aminobutanoic acid

By proceeding as in Example 1, but replacing the 2-(5-isopropyl)benzofurylcarbaldehyde in stage A of Example 1 by 2-(4,5-dichloro)furylcarbaldehyde, there are obtained:
in STAGE C: 4-(2-(4,5-dichlorofuryl))-2-oxopyrrolidine,
and in STAGE D: the title compound.

EXAMPLE 25

3-(2-(4-methoxybenzothienyl))-4-aminobutanoic acid

By proceeding as in Example 9, but using initially in stage A of Example 9 2-(4-methoxy)benzothienylcarbaldehyde, there are obtained:
in STAGE C: 4-(2-(4-methoxybenzothienyl))-2-oxopyrrolidine,
in STAGE D: 1-tert.-butoxycarbonyl-2-oxo-4-(2-(4-methoxybenzothienyl))pyrrolidine,
and in STAGE F: the title compound.

EXAMPLE 26

3-(2-imidazolyl)-4-acetylaminobutanoic acid methyl ester 0.01 mol of the compound obtained in stage B of Example 16 is dissolved in 50 cm$^3$ of chloroform. 0.01 mol of acetic anhydride and 0.015 mol of sodium carbonate are added. The whole is heated under reflux for five hours while stirring. The reaction mixture is then cooled, evaporated to dryness and extracted with chloroform twice. The chloroform phases are combined and dried over calcium chloride and the solvent is evaporated in vacuo on a water bath. The residue is purified by chromatography.

EXAMPLE 27

3-(2-(4-methoxyfuryl))-4-aminobutanoic acid

By proceeding as in Example 1, but using 2-(4-methoxy)furylcarbaldehyde in stage A of Example 1 instead of 2-(5-isopropyl)benzofurylcarbaldehyde, there are obtained:
in STAGE C: 4-(2-(4-methoxyfuryl))-2-oxopyrrolidine,
and in STAGE D: the title compound.

EXAMPLE 28

3-(4-pyridazinyl)-4-aminobutanoic acid

By proceeding as in Example 1, but using 4-pyridazinylcarbaldehyde in stage A of Example 1 instead of 2-(5-isopropyl)benzofurylcarbaldehyde, there are obtained:
in STAGE C: 4-(4-pyridazinyl)-2-oxopyrrolidine,
and in STAGE D: the title compound.

EXAMPLE 29

3-(2-pyrimidinyl)-4-aminobutanoic acid

By proceeding as in Example 1, but using 2-pyrimidinylcarbaldehyde in stage A of Example 1 instead of 2-(5-isopropyl)benzofurylcarbaldehyde, there are obtained:
in STAGE C: 4-(2-pyrimidinyl)-2-oxopyrrolidine,
and in STAGE D: the title compound.

EXAMPLE 30

3-(2-benzimidazolyl)-4-aminobutanoic acid

By proceeding as in Example 1, but using 2-benzimidazolylcarbaldehyde in stage A of Example 1 instead of 2-(5-isopropyl)benzofurylcarbaldehyde, there are obtained:
in STAGE C: 2-(2-benzimidazolyl)-2-oxopyrrolidine,
and in STAGE D: the title compound.

EXAMPLE 31

3-(3-azepinyl)-4-aminobutanoic acid

By proceeding as in Example 1, but using 3-azepinylcarboxaldehyde in stage A of Example 1 instead of 2-(5-isopropyl)benzofurylcarbaldehyde, there are obtained:
in STAGE C: 4-(3-azepinyl)-2-oxopyrrolidine,
and in STAGE D: the title compound.

EXAMPLE 32

3-(3-(1,4-diazepinyl))-4-aminobutanoic acid

By proceeding as in Example 1, but using (3-(1,4-diazepinyl))carboxaldehyde in stage A of Example 1 instead of 2-(5-isopropyl)benzofurylcarbaldehyde, there are obtained:
in STAGE C: 4-(3-(1,4-diazepinyl))-2-oxopyrrolidine,
and in STAGE D: the title compound.

EXAMPLE 33

3-(3-benzo[b]azepinyl)-4-aminobutanoic acid

By proceeding as in Example 1, but using (3-benzo[b-]azepinylcarbaldehyde in stage A of Example 1 instead of 2-(5-isopropyl)benzofurylcarbaldehyde, there are obtained:
in STAGE C: 4-(3-benzo[b]azepinyl)-2-oxopyrrolidine,
and in STAGE D: the title compound.

EXAMPLE 34

3-(2-(1,3,5-triazinyl))-4-aminobutanoic acid

By proceeding as in Example 1, but using (2-(1,3,5-triazinyl))carbaldehyde in stage A of Example 1 instead of 2-(5-isopropyl)benzofurylcarbaldehyde, there are obtained:
in STAGE C: 4-(2-(1,3,5-triazinyl))-2-oxopyrrolidine,
and in STAGE D: the title compound.

EXAMPLE 35

3-(2-indolyl)-4-aminobutanoic acid

By proceeding as in Example 9, but using initially in stage A of Example 9 2-indolylcarbaldehyde, there are obtained:

STAGE C: 4-(2-indolyl)-2-oxopyrrolidine,
STAGE D: 1-tert.-butoxycarbonyl-2-oxo-4-(2-indolyl)pyrrolidine,
and in STAGE F: the title compound.

EXAMPLE 36

3-(2-(5-methoxyindolyl))-4-aminobutanoic acid

By proceeding as in Example 9, but using initially in stage A of Example 9 2-(5-methoxy)indolylcarbaldehyde, there are obtained:

STAGE C: 4-(2-(5-methoxyindolyl))-2-oxopyrrolidine,
STAGE D: 1-tert.-butoxycarbonyl-2-oxo-4-(2-(5-methoxyindolyl))pyrrolidine,
and in STAGE F: the title compound.

EXAMPLE 37

3-(2-(5-methylindolyl))-4-aminobutanoic acid

By proceeding as in Example 9, but using initially in stage A of Example 9 2-(5-methyl)indolylcarbaldehyde, there are obtained:

STAGE C: 4-(2-(5-methylindolyl))-2-oxopyrrolidine,
STAGE D: 1-tert.-butoxycarbonyl-2-oxo-4-(2-(5-methylindolyl))pyrrolidine,
and in STAGE F: the title compound.

EXAMPLE 38

3-(2-(5-chloroindolyl))-4-aminobutanoic acid

By proceeding as in Example 9, but using initially in stage A of Example 9 2-(5-chloro)indolylcarbaldehyde, there are obtained:

STAGE C: 4-(2-(5-chloroindolyl))-2-oxopyrrolidine,
STAGE D: 1-tert.-butoxycarbonyl-2-oxo-4-(3-(5-chloroindolyl))pyrrolidine,
and in STAGE F: the title compound.

EXAMPLE 39

4-tert.-butoxycarbonylamino-3-(2-(5-methoxybenzofuryl))butanoic acid

By proceeding as in Example 9, but initially using 2-(5-methoxy)benzofurylcarbaldehyde in Stage A of Example 9, there is obtained:

in STAGE D: 1-tert.-butoxycarbonyl-2-oxo-4-(2-(5-methoxybenzofuryl))pyrrolidine
Melting point: 90°-92° C.
Spectral characteristics:
infrared: 1710-1740 cm$^{-1}$: $\sigma$CO
NMR (CDCl$_3$):
$\delta$: 1.53 ppm: singlet: (C(CH$_3$)$_3$)
$\delta$: 2.87 ppm: doublet: (CH$_2$CO)
$\delta$: 3.83 ppm: multiplet: (CH$_3$O, CH, CH$_2$ N)
$\delta$: 6.48 ppm: singlet: (H$_3$'; benzofuran)
$\delta$: 6.87 ppm: doublet: (H$_6$'; benzofuran)
$\delta$: 7.00 ppm: doublet: (H$_4$'; benzofuran)
$\delta$: 7.44 ppm: doublet: (H$_7$'; benzofuran)
and in STAGE E: the title product:
Melting point: 149°-153° C.
Spectral characteristics:
infrared: 1700-1720 cm$^{-1}$: $\sigma$CO
3420 cm$^{-1}$: $\sigma$NH NMR (CDCl$_3$):
$\delta$: 1.40 ppm: singlet: (C(CH$_3$)$_3$)
$\delta$: 2.70-2.90 ppm: multiplet: (CH$_2$CO)
$\delta$: 3.40-3.70 ppm: multiplet: (CH$_2$N, CH)
$\delta$: 3.82 ppm: singlet: (CH$_3$O)
$\delta$: 4.70 ppm: singlet: (NH)
$\delta$: 6.45 ppm: singlet: (H$_3$'; benzofuran)
$\delta$: 6.82 ppm: doublet: (H$_6$'; benzofuran)
$\delta$: 6.95 ppm: doublet: (H$_4$'; benzofuran)
$\delta$: 7.33 ppm: doublet: (H$_7$'; benzofuran)

EXAMPLE 40

4-tert.-butoxycarbonylamino-3-(2-(5-methoxybenzofuryl))butanamide

STAGE A: 4-tert.-butoxycarbonylamino-3-(2-(5-methoxybenzofuryl))butanamide acid chloride By proceeding as in stage A of Example 16, but replacing the 3-(2-imidazolyl)-4-aminobutyric acid by the compound of Example 39, the product of stage A is obtained.

STAGE B: 4-tert.-butoxycarbonylamino-3-(2-(5-methoxybenzofuryl))butanamide

By proceeding as in Example 17, but replacing the 3-(2-imidazolyl)-4-aminobutanoic acid chloride by the compound obtained in stage A of Example 40, the title product is obtained:
Melting point: 175°-177° C.
Spectral characteristics:
infrared: 1665-1700 cm$^{-1}$: $\sigma$CO
3400 cm$^{-1}$: $\sigma$NH

PHARMACOLOGICAL STUDY OF THE COMPOUNDS OF THE INVENTION

EXAMPLE 41

Acute Toxicity Study

Acute toxicity was assessed after the oral administration to groups of 5 mice (20±2 grams) of increasing doses (0.05; 0.1; 0.25; 0.50; 0.75 g/kg). The animals were observed at regular intervals over the course of the first day and daily for the two weeks following treatment.

It appears that the compounds of the invention are atoxic.

EXAMPLE 42

Study of the Affinity to GABA$_B$ Receptors

This study was carried out in accordance with conventional binding study techniques.

It appears that the compounds of the invention have a very strong affinity to GABA$_B$ receptors.

Thus, some of the compounds of the invention have an IC$_{50}$ of 0.05 $\mu$M in the presence of R(−) [$^3$H] baclofen. By way of comparison, the best compound of the prior art having a similar structure (J. Med. Chem. 1987, 30, 743-746) had an IC$_{50}$ in this test of 0.61 $\mu$M and baclofen had an IC$_{50}$ of 0.33 $\mu$M.

EXAMPLE 43

Study of the Inhibition of Excitation Activity Induced by Convulsants

The compounds of the invention antagonise the excitatory activity induced by convulsants in hippocampal preparations.

Hippocampal preparations were prepared from the brains of sacrificed adult female rats. Transverse sections were placed in a preservative medium. After 1 hour and 30 minutes' incubation, the isolated preparations were placed under registration, perfused with a saline solution and oxygenated. Spontaneous potentials appear which are associated with CA3 pyramidal cells. Excitation is induced by the addition of bicucullin (50 μM).

The compounds of the invention, at various concentrations, or baclofen are then added.

The baclofen or the compounds of the invention are perfused for periods of 10 minutes. The excitation rate is calculated during the four minutes preceding the perfusion of baclofen or the compounds of the invention and during the last four minutes of the perfusion of the products to be studied.

The inhibition is expressed as percentage excitation in relation to the initial rate, which permits the determination of an inhibiting concentration 50 ($IC_{50}$).

The compounds of the invention have an $IC_{50}$ of from 5 to 20 μM; baclofen in this test has an $IC_{50}$ of approximately 50 μM.

EXAMPLE 44

Stimulation of the Synthesis of Cyclic AMP in the Brain

The compounds to be tested are administered intraperitoneally at a dose of 10 mg/kg to mice of the OF1-/IFFA Credo strain. 24 hours after the last injection, the animals are sacrificed by freezing, the cAMP present in these cerebral structures is dosed by radioimmunology according to Amersham's method (specific binding protein). Some of the compounds of the invention appear to be capable of greatly increasing the cerebral synthesis of cyclic AMP.

EXAMPLE 45

Pharmaceutical Composition: Tablets

Tablets each containing 1.5 mg of 3-(2-imidazolyl)-4-aminobutanoic acid.

Formula for 1000 tablets:

| | |
|---|---|
| 3-(2-imidazolyl)-4-aminobutanoic acid | 1.5 g |
| wheat starch | 15 g |
| cornstarch | 15 g |
| lactose | 90 g |
| magnesium stearate | 2 g |
| silica | 1 g |
| hydroxypropylcellulose | 2 g |

We claim:

1. A compound selected from those of formula (I):

in which:
  $R_1$ represents hydroxy, amino, lower alkylamino, lower alkoxy, or halogen,
  $R_2$ represents hydrogen, lower alkyl, lower acyl, or lower alkoxycarbonyl,
  R represents:
    a radical of the formula

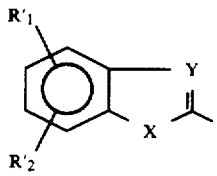

in which:
  X represents oxygen or sulphur,
  Y represents —CH—,
  $R'_1$ and $R'_2$, which are identical or different, represent halogen, hydrogen, lower alkyl, lower alkoxy, hydroxy, nitro, amino, lower alkylamino, or trifluoromethyl, with the proviso that, when X is an oxygen, Y is —CH— and each of $R'_1$ and $R_2$ is hydrogen, then $R'_2$ can not represent hydrogen, lower-alkoxy, or methoxy,
  a radical of the formula

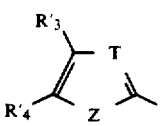

in which:
  Z represents oxygen, or sulphur,
  T represents —CH—,
  $R'_3$ and $R'_4$, which are identical or different, represent a radical selected from hydrogen, halogen, lower alkyl, lower alkoxy, hydroxy, nitro, amino, lower alkylamino, and trifluoromethyl, with the proviso that, when Z is sulphur, T is —CH—, and one of $R'_3$ and $R'_4$ is hydrogen, then the other of $R'_3$ and $R'_4$ may not be hydrogen, chlorine, bromine, methyl, or ethyl and that, when Z is an oxygen, T is —CH—, and one of $R'_3$ and $R'_4$ is hydrogen, then the other of $R'_3$ and $R'_4$ may not be hydrogen or lower-alkyl,
  its optical isomers and also, where appropriate, its salts of addition with a pharmaceutically acceptable base or acid,
  the terms "lower alkyl", "lower alkoxycarbonyl", "lower alkoxy", "lower alkylamino" and "lower acyl" indicate a group containing 1 to 6 carbon atoms inclusive in a straight or branched chain.

2. A compound according to claim 1 in which R represents a radical of the formula:

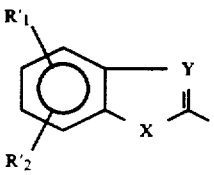

in which $R'_1$, $R'_2$, X and Y are as defined in claim 1.

3. A compound according to claim 1, in which R represents a radical of the formula:

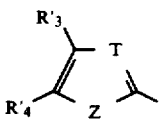

in which Z, T, R′₃ and R′₄ are as defined in claim 1.

4. A compound according to claim 1, in which R is a radical of the formula:

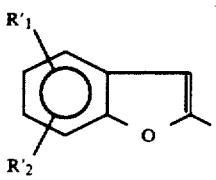

in which R′₁ and R′₂, which are identical or different, represent halogen, hydrogen, lower alkyl, lower alkoxy, or trifluoromethyl, with the proviso that, when R′₁ and R′₂ are hydrogen, R′₂ can not represent hydrogen, lower-alkoxy, or methyl.

5. A compound according to claim 1, in which R is a radical of the formula:

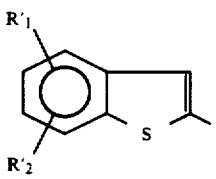

in which R′₁ and R′₂, which are identical or different, represent hydrogen, halogen, lower alkyl, lower alkoxy or trifluoromethyl.

6. A compound according to claim 1, in which R represents a group:

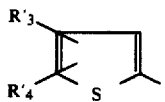

in which R′₃ and R′₄, which are identical or different, represent a radical selected from hydrogen, halogen, lower alkyl, lower alkoxy, and trifluoromethyl, with the proviso that, if R′₃ and R′₄ is hydrogen, then the other of R′₃ and R′₄ may not be hydrogen, chlorine, bromine, methyl or ethyl.

7. A compound according to claim 1, in which R represents a group:

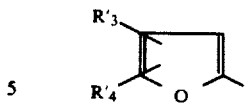

in which R′₃ and R′₄, which are identical or different, represent a radical selected from hydrogen, halogen, lower alkyl, lower alkoxy, and trifluoromethyl, with the proviso that, if R′₃ is hydrogen, then R′₄ may not be hydrogen or lower-alkyl.

8. A compound according to claim 1 which is selected from 3-(2-(5-isopropylbenzofuryl))-4-aminobutanoic acid, its isomers and a salt of addition thereof with a pharmaceutically-acceptable acid or base.

9. A compound according to claim 1 which is selected from 3-(2-(5-ethylbenzofuryl))-4-aminobutanoic acid, its isomers and a salt of addition thereof with a pharmaceutically-acceptable acid or base.

10. A compound according to claim 1 which is selected from 3-(2-(5-(1-methylpropyl)benzofuryl))-4-aminobutanoic acid, its isomers and a salt of addition thereof with a pharmaceutically-acceptable acid or base.

11. A compound according to claim 1 which is 3-(2-(5-fluorobenzofuryl))-4-aminobutanoic acid, its isomers and a salt of addition thereof with a pharmaceutically-acceptable acid or base.

12. A compound according to claim 1 which is selected from 3-(2-(4,5-dichlorothienyl))-4-aminobutanoic acid, its isomers and a salt of addition thereof with a pharmaceutically-acceptable acid or base.

13. A compound according to claim 1 which is selected from 3-(2-(5-chlorobenzofuryl))-4-aminobutanoic acid, its isomers and a salt of addition thereof with a pharmaceutically-acceptable acid or base.

14. A compound according to claim 1 which is selected from 3-(2-benzothienyl))-4-aminobutanoic acid, its isomers and a salt of addition thereof with a pharmaceutically-acceptable acid or base.

15. A pharmaceutical composition useful in treating a disorder related to a dysfunction of GABA$_B$ receptors, including spastic disorders and senescence disorders, containing as active principle an effective amount of a compound as claimed in claim 1 in combination with a pharmaceutically-acceptable excipient or vehicle.

16. A method for treating a living animal afflicted with disorders related to a dysfunction of GABA$_B$ receptors, including spastic disorders and senescence disorders, comprising the step of administering to the said living animal an amount of a compound of claim 1 which is effective for alleviation of said condition.

* * * * *

UNITED STATES PATENT AND TRADEMARK OFFICE
CERTIFICATE OF CORRECTION

PATENT NO. : 5,162,364

DATED : Nov. 10, 1992

INVENTOR(S) : Michel Debaert, Pascal Berthelot, Claude Vaccher

It is certified that error appears in the above-identified patent and that said Letters Patent is hereby corrected as shown below:

Column 4, line 8; "halo9en" should read -- halogen --.

Column 7, line 3; "0 05" should read -- 0.05 --.

Column 7, line 24; "$cm^{-1}$: o CO" should read -- $cm^{-1}: \nu$ CO --

Column 7, line 25; "$m^{-1}$: o NH" should read -- $m^{-1}:\nu$ NH --.

Column 7, approximately line 51; "$cm^{-1}$: o CO" should read -- $cm^{-1}: \nu$ CO --.

Column 7, approximately line 52; "$cm^{-1}$: o OH" should read -- $cm^{-1}: \nu$ OH --.

Column 8, line 5; "$cm^{-1}$: o CO" should read -- $cm^{-1}: \nu$ CO --.

Column 8, line 6; "$m^{-1}$: o NH" should read -- $m^{-1}: \nu$ NH --

Column 8, line 19; "$cm^{-1}$; o CO" should read -- $cm^{-1}: \nu$ CO --.

Column 8, line 20; "$cm^{-1}$: o (COO-," should read -- $cm^{-1}: \nu$ (COO-,--.

Column 8, approximately line 40; "$cm^{-1}$: o CO 3200 $m^{-1}$: o NH" should read -- $cm^{-1}: \nu$ CO 3200 $m^{-1}:$ NH --.

Column 8, line 54; "$cm^{-1}$: o CO" should read -- $cm^{-1}: \nu$ CO --.

Column 8, line 55; "$cm^{-1}$: o OH" should read -- $CM^{-1}: \nu$ OH --.

Column 9, line 8; "$cm^{-1}$; o CO" should read -- $cm^{-1}: \nu$ CO --.

Column 9, line 9; "$m^{-1}$: o NH" should read -- $m^{-1}:\nu$ NH --.

Column 9, line 23; "$cm^{-1}$: o CO 2300-3200 $cm^{-1}$: o OH" should read -- $cm^{-1}: \nu$ CO 2300-3200 $cm^{-1}:\nu$ OH --.

Column 9, approximately line 27; "3-(2 (5-" should read -- 3-(2-(5- --.

Column 9, line 44; "$cm^{-1}$: o CO" should read -- $cm^{-1}: \nu$ CO --.

Column 9, line 45; " $m^{-1}$: o NH: should read -- $m^{-1}: \nu$ NH --.

UNITED STATES PATENT AND TRADEMARK OFFICE
CERTIFICATE OF CORRECTION

PATENT NO. : 5,162,364

DATED : Nov. 10, 1992

INVENTOR(S) : Michel Debaert, Pascal Berthelot, Claude Vaccher

It is certified that error appears in the above-identified patent and that said Letters Patent is hereby corrected as shown below:

Column 9, line 56; "$cm^{-1}$: o CO 2300-3200 $cm^{-1}$: o OH" should read -- $cm^{-1}$: $\nu$ CO 2300-3200 $cm^{-1}$: $\nu$ OH --.

Column 10, approximately line 16; "$cm^{-1}$: o CO" should read -- $cm^{-1}$: $\nu$ CO --.

Column 10, approximately line 17; "$cm^{-1}$: o OH" should read -- $cm^{-1}$: $\nu$ OH --.

Column 10, approximately line 49; "$cm^{-1}$: o CO" should read -- $cm^{-1}$: $\nu$ CO --.

Column 11, line 5; "$cm^{-1}$: o NH" should read -- $CM^{-1}$: $\nu$ NH --.

Column 11, line 5/6; after line 11 ending "NH" and before line 12 beginning "NMR" insert -- 1700 $cm^{-1}$: $\nu$ CO --.

Column 11, line 21; "$cm^{-1}$: o (COO-," should read --$cm^{-1}$: $\nu$ (COO-,--.

Column 11, line 22; "$cm^{-1}$: o CO" should read --$cm^{-1}$: $\nu$ CO --.

Column 11, approximately line 58; "$cm^{-1}$: o NH" should read -- $cm^{-1}$: $\nu$ NH --.

Column 11, approximately line 59; "$cm^{-1}$: o CO" should read -- $cm^{-1}$: $\nu$ CO --.

Column 11, line 60; "$cm^{-1}$: o CO" should read --$cm^{-1}$: $\nu$ CO--.

Column 12, line 27; "$cm^{-1}$: o (COO," should read --$cm^{-1}$: $\nu$ (COO-, --.

Column 12, line 28; "$cm^{-1}$: o CO" should read --$cm^{-1}$: $\nu$CO --.

Column 12, line 29; "NMR ($D_2$):" should read -- NMR ($D_2O$): --.

Column 12, line 31; "($\underline{CH}$-$\underline{CH}$-$NH_2$)" should read --($\underline{CH}$ -$\underline{CH}_2$-$NH_2$) --.

UNITED STATES PATENT AND TRADEMARK OFFICE
CERTIFICATE OF CORRECTION

PATENT NO. : 5,162,364

DATED : Nov. 10, 1992

INVENTOR(S) : Michel Debaert, Pascal Berthelot, Claude Vaccher

It is certified that error appears in the above-identified patent and that said Letters Patent is hereby corrected as shown below:

Column 12, approximately line 45; "$cm^{-1}$: o (COO-," should read -- $cm^{-1}$: ν (COO-, --.

Column 12, line 46; "$cm^{-1}$: o CO" should read --$cm^{-1}$: ν CO--.

Column 12, line 61; "$cm^{-1}$: o CO" should read --$cm^{-1}$: ν CO --

Column 12, line 62; "$cm^{-1}$: o NH" should read -- $cm^{-1}$:νNH --.

Column 12, line 67; move the "$_2$__" from the beginning of line 67 to the end of line 66.

Column 13, line 10; "$cm^{-1}$: o (COO-," should read --$cm^{-1}$:ν (COO-,--.

Column 13, line 11; "$cm^{-1}$: o CO" should read --$cm^{-1}$: ν CO --.

Column 14, line 12; "0 01 mol" should read --0.01 mol --.

Column 17, line 55; "$cm^{-1}$: o CO" should read --$cm^{-1}$: ν CO --.

Column 17, line 67; "$cm^{-1}$: o CO" should read --$cm^{-1}$: ν CO --.

Column 17, line 68; "$cm^{-1}$: o NH" should read --$cm^{-1}$: ν NH --.

Column 18, approximately line 29; "$cm^{-1}$: o CO" should read -- $cm^{-1}$:ν CO --.

Column 18, line 30; "$cm^{-1}$: o NH" should read -- $cm^{-1}$:ν NH --.

Column 20, approximately line 21; "or methoxy," should read -- or methyl, --.

Column 20, approximately line 41; "Z is an oxygen," should read --Z is oxygen,--.

Column 21, approximately line 37/38; "alkoxy or" should read -- alkoxy, or --.

UNITED STATES PATENT AND TRADEMARK OFFICE
CERTIFICATE OF CORRECTION

PATENT NO. : 5,162,364

DATED : Nov. 10, 11992

INVENTOR(S) : Michle Debaert, Pascal Berthelot, Claude Vaccher

It is certified that error appears in the above-identified patent and that said Letters Patent is hereby corrected as shown below:

Column 21, line 51; "if $R'_3$" should read -- if one of $R'_3$ --.

Column 22, line 50; "with disorders related to" should read -- with a disorder related to --.

Signed and Sealed this

First Day of March, 1994

Attest:

BRUCE LEHMAN

Attesting Officer

Commissioner of Patents and Trademarks